United States Patent
Ledoux et al.

(10) Patent No.: US 10,143,390 B2
(45) Date of Patent: Dec. 4, 2018

(54) METHOD AND APPARATUS TO AUTOMATICALLY DETERMINE THE RELATIONSHIP BETWEEN DATA

(71) Applicant: Pie Medical Imaging B.V., Maastricht (NL)

(72) Inventors: Leon Ledoux, Landgraaf (NL); Bas Weijers, Maasmechelen (BE); Jean-Paul Aben, Limbricht (NL)

(73) Assignee: Pie Medical Imaging B.V., Maastricht (NL)

( * ) Notice: Subject to any disclaimer, the term of this patent is extended or adjusted under 35 U.S.C. 154(b) by 52 days.

(21) Appl. No.: 15/491,844

(22) Filed: Apr. 19, 2017

(65) Prior Publication Data
US 2017/0311821 A1  Nov. 2, 2017

(30) Foreign Application Priority Data
May 2, 2016 (EP) .................................. 16167909

(51) Int. Cl.
*G06K 9/00* (2006.01)
*A61B 5/026* (2006.01)
(Continued)

(52) U.S. Cl.
CPC .......... *A61B 5/0263* (2013.01); *A61B 5/7225* (2013.01); *G01R 33/563* (2013.01);
(Continued)

(58) Field of Classification Search
None
See application file for complete search history.

(56) References Cited

U.S. PATENT DOCUMENTS

| | | |
|---|---|---|
| 6,252,402 B1 | 6/2001 | Sanfilippo et al. |
| 7,332,912 B2 | 2/2008 | Pittaluga et al. |
| | (Continued) | |

FOREIGN PATENT DOCUMENTS

WO  WO 2015/089222 A2  6/2015

OTHER PUBLICATIONS

"4D Flow Cardiovascular Magnetic Resonance Consensus Statement," Dyverfeldt et al., Journal of Cardiovascular Magnetic Resonance, 2015. 17(1): p. 72.
(Continued)

*Primary Examiner* — Sean M Conner
(74) *Attorney, Agent, or Firm* — Gordon & Jacobson, P.C.

(57) ABSTRACT

A method is provided that determines velocity encoding direction of volumetric image data sets comprising three-directional velocity information (V0, V1, V2) of a target volume, which involves:
a) defining a coordinate system (X, Y, Z);
b) determining all the possible arrangements of the three velocity components (V0, V1, V2) along the three coordinate axes (X, Y, Z);
c) determining reference point or points in the target volume either automatically or upon user input;
d) determining streamlines for each point for all possible combinations of velocity components as determined in b); and
e) considering as velocity encoding direction the arrangement of the three velocity components corresponding to the streamlines having the longest length or a length above a threshold.

A corresponding apparatus and computer program are also disclosed.

16 Claims, 9 Drawing Sheets

(51) Int. Cl.
G06T 7/246 (2017.01)
A61B 5/00 (2006.01)
G01R 33/563 (2006.01)
G06T 7/00 (2017.01)
G01R 33/56 (2006.01)

(52) U.S. Cl.
CPC ... *G01R 33/5608* (2013.01); *G01R 33/56316* (2013.01); *G06T 7/0012* (2013.01); *G06T 7/246* (2017.01); *G06T 2207/10088* (2013.01)

(56) References Cited

U.S. PATENT DOCUMENTS

| | | | |
|---|---|---|---|
| 2009/0161934 A1* | 6/2009 | Zhao | G01R 33/56316 382/131 |
| 2014/0316251 A1* | 10/2014 | Walker-Samuel | G01R 33/56316 600/419 |
| 2015/0061671 A1* | 3/2015 | Greiser | G01R 33/56316 324/309 |
| 2015/0141826 A1 | 5/2015 | Beymer et al. | |
| 2015/0338490 A1* | 11/2015 | Greiser | G01R 33/385 324/309 |

OTHER PUBLICATIONS

"Cardiothoracic Magnetic Resonance Flow Imaging," Hope et al., J Thorac Imaging Jul. 2013; 28(4): 217-30.
"Comprehensive 4D Velocity Mapping of the Heart and Great Vessels by Cardiovascular Magnetic Resonance," Markl et. al., Journal of Cardiovascular Magnetic Resonance, 2011, 13(7).
"Improved aortic pulse wave velocity assessment from multislice two-directional in-plane velocity-encoded magnetic resonance imaging," Westenberg et. al., Journal of Magnetic Resonance Imaging, 2010, 32:1086-1094.
"New Respiratory Gating Technique for Whole Heart Cine Imaging: Integration of a Navigator Slice in Steady State Free Precession Sequences," Uribe et. al., Journal of Magnetic Resonance Imaging 34:211-219 (2011).
"Numerical Recipes in C: The Art of Scientific Computing," Press, William H. et al, 1992 4.2:136-139, Cambridge University Press.
"Robust Learning-Based Parsing and Annotation of Medical Radiographs", Yimo Tao et al., IEEE Transactions on Medical Imaging, vol. 30, No. 2, Feb. 1, 2011, pp. 338-350.
"Time-Resolved 3D MR Velocity Mapping at 3T: Improved Navigator-Gated Assessment of Vascular Anatomy and Blood Flow," Markl et. al., Journal of Magnetic Resonance Imaging, 2007, 25: 824-831.
"Time-Resolved Three-Dimensional Phase-Contrast MRI", Markl et al, Journal of Magnetic Resonance Imaging, 2003, 17:499-506.

* cited by examiner

METHOD AND APPARATUS TO AUTOMATICALLY DETERMINE THE RELATIONSHIP BETWEEN DATA

CROSS-REFERENCE TO RELATED APPLICATIONS

The present application claims priority from EP16167909.7, filed on May 2, 2016, entitled "A METHOD AND APPARATUS TO AUTOMATICALLY DETERMINE THE RELATIONSHIP BETWEEN DATA," herein incorporated by reference in its entirety.

BACKGROUND

1. Field

The invention relates to the technical field of medical imaging, particularly MR cardiovascular imaging, although it can find application in any field where there is the need to quantify flow in volumetric image data sets that comprise structural information and three directional velocity information.

2. State of the Art

Pulsatile blood flow through the cavities of the heart and vascular system is multidirectional and multidimensional where the flow varies over time during the cardiac cycle. Traditionally, magnetic resonance imaging (MRI) of flow using phase contrast (PC) methods is accomplished using methods that resolve single-directional flow in two spatial dimensions (2D) of an individual slice. This single velocity encoding direction is typically selected perpendicular to the 2D plane, which enables calculation of the volume of flow passing through that 2D slice, but is unable to assess the multidirectional and multidimensional flow.

Formerly the common clinical tool for cardiovascular flow assessment was Doppler echocardiography, which could measure the blood flow velocity component in the direction of the ultrasound beam or provide a 2D visualization of one-directional blood flow velocities using the color Doppler mode. This technique is however limited due to variable velocity assessment (due to beam alignment), limited acoustic window, and operator expertise.

Furthermore, the calculation of mean velocities and net flow is often based on assumptions regarding the underlying flow profile and vessel cross-sectional area which may result in inaccurate flow quantification in the presence of complex flow and/or vessel geometry.

At the moment, the most common contrast MR flow imaging technique is 2D cine phase contrast MR with velocity encoding in a single direction. This single velocity encoding direction is typically selected perpendicular to the 2D plane, which enables calculation of the volume of flow passing through that 2D plane.

More recently, time resolved three-dimensional (3D) phase contrast MRI (here termed four-dimensional (4D) MR Flow) has drawn increased attention. In 4D MR flow, anatomical and three-directional velocity information are acquired for each voxel within a 3D volume over time and offers the ability to measure and to visualize the temporal evolution of blood flow patterns within an acquired 3D volume. 4D MR Flow data encompassing individual vascular structures and entire vascular territories such as the heart, the adjacent aorta, the carotid arteries, abdominal, or peripheral vessels. 4D MR Flow allows the comprehensive evaluation of complex blood flow patterns in individual vascular structures and entire vascular territories such as the heart, the adjacent aorta, the carotid arteries, abdominal, or peripheral vessels. This unique technique enables a wide variety of options for visualization and quantification of flow, ranging from basic aspects such as the quantification of pump blood volume as well as the estimation of hemodynamic effects at the vessel wall, visualization of flow pathways in the heart and the cardiovascular system as reported by Hope e.t al., "*Cardiothoracic Magnetic Resonance Flow Imaging*," J Thorac Imaging 2013 July; 28(4): 217-30.

4D MR Flow data acquisition can be achieved using different image acquisition methods, for instance as reported by Markl et. al., "*Time Resolved 3D MR Velocity Mapping at 3T: Improved Navigator-Gated Assessment of Vascular Anatomy and Blood Flow*," J Magn Reson Imaging 2007; 25: 824-831. The 4D MR Flow acquisitions results in a 3D anatomical volume in which each voxel includes velocity information in all three dimensions (x-, y-, z-direction). After the data acquisition is completed, the acquired data yields 3D time resolved magnitude data (anatomical images) and three time series representing the three-directional blood flow velocities Vx, Vy, and Vz (velocity images).

The acquired 4D MR Flow data is stored before data interpretation and subsequent analysis into a standardized data format; DICOM. DICOM stands for 'Digital Imaging and Communication in medicine' and is a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, servers, workstations, printers, and network hardware from multiple manufacturers into a Picture Archiving and Communication System (PACS). The different devices come with DICOM conformance statements which clearly state which DICOM classes they support. DICOM has been widely adopted by hospitals.

The most important DICOM information is the sequence of numbers describing the image data itself. The image information is also introduced by an identical tag. Since there are different methods for the numeric interpretation of the pixels of an image, the DICOM information should contain data about the interpretation.

All manufacturers of MR imaging systems will export the acquired image data in a standardized file format according to the DICOM standard. This DICOM standard is establish with the contribution of the imaging manufactures and provides a detailed specification that describes the means of formatting and exchanging medical images and associated information by for handling, storing, printing, and transmitting information in medical imaging. The DICOM standard prescribes for each image modality the information which is minimum required for a correct interpretation of the image data. The standard allows freedom to include additional information and most of the imaging manufacturers store additional information which is not prescribed by the DICOM standard and may communicate this by their DICOM Conformance Statements.

For the correct interpretation of the 4D MR Flow data, several information in DICOM is used. For instance the 'Velocity Encoding Direction' is required, which encloses the direction cosines of the velocity encoding vector with respect to the patient. This information must be available for each of the velocity encoding images that corresponds to the velocity encoding direction (x-, y-, and z-direction). Although the DICOM standard provides a uniform way to store medical images including patient and imaging modality specific information, not all information required for image data analysis is prescribed. This especially is true for new imaging methods, such as time-resolved three-dimensional phase contrast MM (4D MR Flow) as identified in the recent 4D Flow consensus paper by Dyverfeldt et. al., "*4D flow cardiovascular magnetic resonance consensus statement*," J Cardiovasc Magn Reson, 2015. 17(1): p. 72.

Before storing the 4D MR Flow data it is in the interest of patient confidentiality to remove all information identifying the patient from the DICOM header when a DICOM file is downloaded from a PACS to an external system, as for instance to a diagnostic workstation or at a Web client.

Normally, the information about the order and the flow encoding direction of the acquired velocity components is stored in the DICOM, but in some case this information is missing. For instance, some MR manufacturers do not fully comply with the prescribed DICOM standard or place the information in private DICOM objects. Furthermore, if images are transferred through different systems, such as PACS, anonymize tools, information belonging to the image may be removed.

When the information about the order and the flow encoding direction of the acquired velocity components is missing, the 4D MR Flow becomes useless for, for instance, flow visualization and quantification.

The need is therefore for a method that can be applied to determine the order and the flow direction of the velocity components for situations where the velocity directional information is missing.

The invention proposes a method/workflow to extract the relationship of the 4D MR Flow data, and enhancing significantly the usability of 4D MR Flow quantitative analysis of cardiovascular blood flow as well as the visualization of cardiovascular blood flow.

SUMMARY OF THE INVENTION

It is thus an object of the present invention to extract the relationship of the data to enhance significantly the usability of 4D MR Flow quantitative analysis.

In accordance with embodiments herein, systems, computer program products and computer implemented methods are provided for determining velocity encoding direction of volumetric image data sets comprising three-directional velocity information ($V_0$, $V_1$, $V_2$) of a target volume, typically sequences of 4D MR flow data sets, the systems, program products and methods comprising, under control of one or more computer systems configured with specific executable instructions, which involves:

a) defining a coordinate system (X, Y, Z);
b) determining all the possible arrangements of the three velocity components ($V_0$, $V_1$, $V_2$) along the three coordinate axes (X, Y, Z);
c) determining reference point or points in the target volume either upon user input or automatically, for example by selecting velocity voxels having velocity module $S=|\vec{V}|=\sqrt{V_0^2+V_1^2+V_2^2}$ above a velocity threshold or selecting magnitude voxels having magnitude data above a magnitude threshold in case volumetric image data sets comprise structural magnitude information and three-directional velocity information of the target volume;
d) determining streamlines or flow lines (i.e., lines representing a path in the direction of flow) for each point for all possible combinations of velocity components as determined in b); and
e) considering as velocity encoding direction the arrangement of the three velocity components corresponding to the streamlines having the longest length or a length above a threshold.

The streamlines or flow lines of d) can be determined in the peak systolic phase when flow is higher, although they can be calculated in any cardiac phase.

Embodiments provide that flow direction may be used to determine the orientation of the velocity encoding direction. Such flow direction may be an input from the user or automatically calculated. In this case, the arrangement of the three velocity components is advantageously inverted in orientation if the corresponding flow line doesn't follow the flow direction.

Temporal velocity curves in a point upstream (A) and in a point downstream (B) may be advantageously used to determine the flow direction. For example, the flow direction may be considered downstream if the curve at point upstream (A) is delayed in time with reference to the curve at point downstream (B), or the flow direction may be considered upstream if the curve at point downstream (B) is delayed in time with reference to the curve at point upstream (A).

Delay between the curves may be searched, for example, by identifying the peak in the curves and comparing temporal position among such peaks or by calculating a correlation function among the upstream and downstream curves.

The correlation function is given as:

$$CC(T) = \sum_{t=0}^{N_{phases}-1} S_A(t) \cdot S_B(\mathrm{mod}(t+T, N_{phases}))$$

where $S_A$, $S_B$ are, respectively, the velocity curves at upstream point A and at downstream point B, T is the temporal lag between the velocity curves, t is the phase index, i.e. the index identifying a 3D volume within the 4D MR Flow data, and $N_{phases}$ is the number of phases, i.e. the amount of 3D volumes within the 4D MR Flow data, the cross-correlation being calculated at least for three lags, such as, for example, −1, 0, +1, wherein upstream condition is determined if $CV(-1)<CC(0)<CC(+1)$ or downstream condition is determined if $CC(-1)>CC(0)>CC(+1)$.

Once velocity encoding direction is determined, it is possible to perform quantitative flow analysis using the velocity information so determined and/or show streamlines, vector fields, cross sectional flow or other similar parameters.

Embodiments also relate to a computer product directly loadable into the memory of a digital computer and comprising software code portions for performing the disclosed method when the product is run on a computer.

Embodiments also relate to a MM apparatus for acquiring volumetric images, the apparatus comprising an acquisition system for obtaining a cine of consecutive image volumes of a target organ, the apparatus further comprising a processing module programmed for performing the method according to any preceding claim.

Particularly the apparatus is configured to acquire 4D flow images of a volume containing a vessel or a tree of vessels, the processing module being programmed to determine the direction and orientation of the velocity vectors related to the flow within such vessel or vessels with reference to a coordinate system.

In an embodiment, the orientation of velocity vectors is determined by the processing module by calculating pulse wave velocity curves in at least two points of the vessel and determining the temporal shift between such curves.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings.

DETAILED DESCRIPTION OF THE PREFERRED EMBODIMENTS

A magnetic resonance imaging (MM) apparatus comprises an imaging unit configured to carry out sequential imaging. The apparatus applies a radio-frequency magnetic field onto a subject (i.e. patient) placed in a static magnetic field. A magnetic resonance signal generated from the subject is detected due to the application of the radio-frequency magnetic field. Using the detected signals an image is created.

The magnetic resonance imaging apparatus also includes a gradient coil that adds spatial positional information to a magnetic resonance signal by applying a gradient magnetic field onto the subject.

Using different combinations of radiofrequency pulses and gradients, different MRI sequences can be made. An MM pulse sequence is a programmed set of changing magnetic gradients. Different pulse sequences allow the radiologist to image the same tissue in various ways, and combinations of sequences reveal important diagnostic information.

Figure 6:
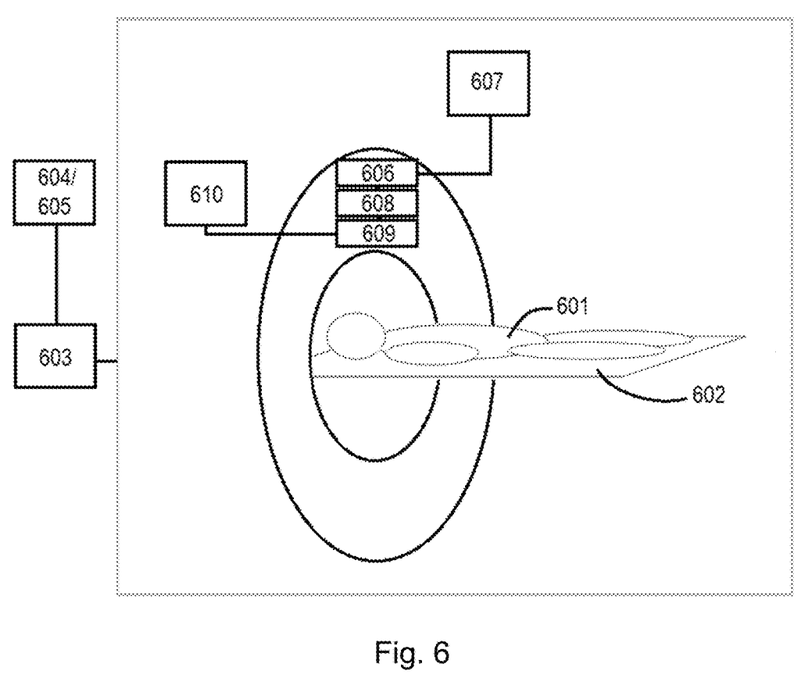
FIG. 6 illustrates an example of a high-level block diagram of an MR system.

FIG. 6 illustrates an example of a high-level block diagram of an MRI system.

Portions of the system (as defined by various functional blocks) may be implemented with dedicated hardware, analog and/or digital circuitry, and/or one or more processors operating program instructions stored in memory.

The MM system of FIG. 6 includes an adjustable table 602 for a patient 601, a data processing module 603 and a magnet system 606.

The data processing module 603 includes one or more processors and memory that stores program instructions to direct the one or more processors to perform the operations described herein. The data processing module 603 also includes a display to present information to a user, such as the images, indicia, data and other information described herein and illustrated in the figures. The data processing module 603 also includes a user interface to receive inputs from the user in connection with operations herein, such as controlling operation of the imaging apparatus. For instance, scan parameters can be selected or altered, patient images may be displayed and post-processing can be performed, including, for example, region of interest measurements, flow quantification and visual and/or quantitative control selecting projection perspectives to be used when obtaining complementary images and the like. The data processing module 603 may correspond to or include portions of one or more of the systems described within the patents and publications referenced herein and incorporated by reference.

One of the key aspects of an MM system is the magnet system 606. The magnet system 606 generally comprises a large tube or a cylindrical magnet. The magnet is typically an electromagnet made from coils of superconducting wire typically helium cooled. The flow of electrical current through these coils produces a magnetic field. Permanent magnets can be used as well. The magnetic field has a certain field strength measured in Tesla. An important aspect of the magnet system 606 is the homogeneity of the magnetic field. That is a magnetic field that changes very little over the specified region or volume.

However, due to manufacturing imperfections or intervention room problems such as nearby steel posts, distortions of the magnetic field may arise. These inhomogeneities are corrected using a shim system 607. The corrections can either be performed manually or automatically. U.S. Pat. Nos. 6,252,402 and 7,332,912 disclose examples of shimming techniques for systems based on permanent magnets.

In clinical Mill hydrogen atoms of the human body are of importance. The nucleus of each hydrogen atom possesses spin also called nuclear spin angular momentum. That is, the nucleus of the hydrogen atom constantly rotates around an axis at a constant rate. When placed inside a magnetic field the nucleus the rotation axis tilts to align with the magnetic field.

The strong static magnetic field produced by the magnet system 606 aligns the spins of each hydrogen atom of the human body in a certain frequency that is dependent on the strength of the magnetic field.

Next, a radio frequency system 609 emits a radio frequency pulse (RF-pulse) towards the part of the body being examined, tuned to a specific range of frequencies at which hydrogen protons move. This results in some of the hydrogen protons being moved 180 degrees out of alignment with the static magnetic field and being forced into phase with other hydrogen protons.

The radio frequency system 609 generally comprises transmitting coils. The transmitting coil is usually built into the body of the scanner and transmits the RF-signal, generating an effective field perpendicular to the main magnetic field.

The energy which is absorbed by different hydrogen atoms in the body is then echoed or reflected back out of the body. The gradient system 608 is switched on and off to measure the echoes reflecting black out of the patient 601 and thus to localize the tissue signals.

Generally, a gradient system 608 consists of one or multiple gradient coils and gradient amplifiers.

Gradient coils are usually loops of wire or thin conductive sheets on a cylindrical shell lying just inside the bore of an MM scanner. When current is passed through these coils a secondary magnetic field is created. This gradient field slightly distorts the main magnetic field in a predictable pattern, causing the resonance frequency of protons to vary as a function of position.

Typically, three sets of gradients are used: the x-, y- and z-gradients. Each coil set is driven by an independent power amplifier and creates a gradient field whose z-component varies linearly along the x-, y- and z-direction respectively producing the orthogonal field distortion required for imaging.

A data acquisition system 610 then receives the echoes. The data acquisition system 610 is responsible for measuring the signals from the protons and digitizing them for later post-processing. In general, the data acquisition system 610 consists of a coil, a pre-amplifier and a signal processing system.

The coil detects the induced voltage form the protons following an RF-pulse. The coil is tuned to the particular frequency of the returning signal.

The pre-amplifier is a low-noise high gain amplifier located inside the magnet room or the coil itself in order to be able to process the signals produced by the protons.

Furthermore, the signal processing system provides for instance further amplification of the signal, demodulation into kHz signal, low-pass filer, divided into real and imaginary parts then detected by the analog-to-digital converters (ADC). By applying an Inverse Fourier transformation (IFT) that converts the signal from the protons as mathematical data (k-space) into a picture that can be interpreted by the clinician.

The storage 604 is used to store the patient images that have been acquired immediately after they have been reconstructed. This is typically done in a universal language (vendor independent) such as DICOM. The storage can be a hard disk or a PACS (picture archiving and communications system) server 605.

Velocity encoding gradient echo imaging, also known as phase contrast imaging, is an MM technique for quantifying blood flow, hereinafter also referenced as 4D MR Flow acquisition. By measuring the phase shift that occurs as protons in the blood move through a magnetic field, the velocity and direction of the blood can be obtained. Details on the time resolved three-dimensional phase contrast MM sequence is published by M. Markl et al, "Time-Resolved Three-Dimensional Phase-Contrast MRI", JMRI 2003 17:499-506. Details on the axial cine MR sequence is published by Uribe et. Al., "New Respiratory Gating Technique for Whole Heart Cine Imaging: Integration of a Navigator Slice in Steady State Free Precession Sequences," Journal of Magnetic Resonance Imaging 34:211-219 (2011).

Figure 7:
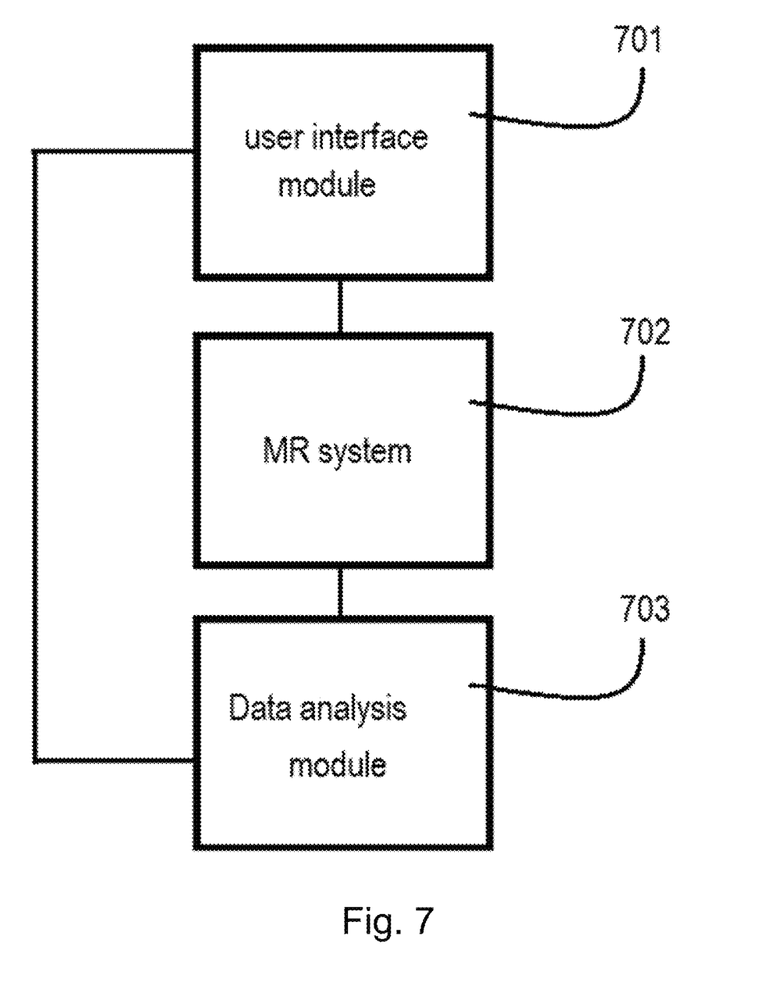
FIG. 7 is a functional block diagram of an exemplary 4D MR Flow acquisition of a MR system in accordance with an embodiment herein.

FIG. 7 is a functional block diagram of an exemplary 4D MR Flow acquisition in accordance to an embodiment herein which includes an MR system 702 that operates under commands from the user interface module and provide data to the data analysis module 703.

A clinician or other user acquires an MRI image of a patient 601 and stores this image on a hard disk 604 or a PACS server 605 in DICOM format.

Figure 1A:
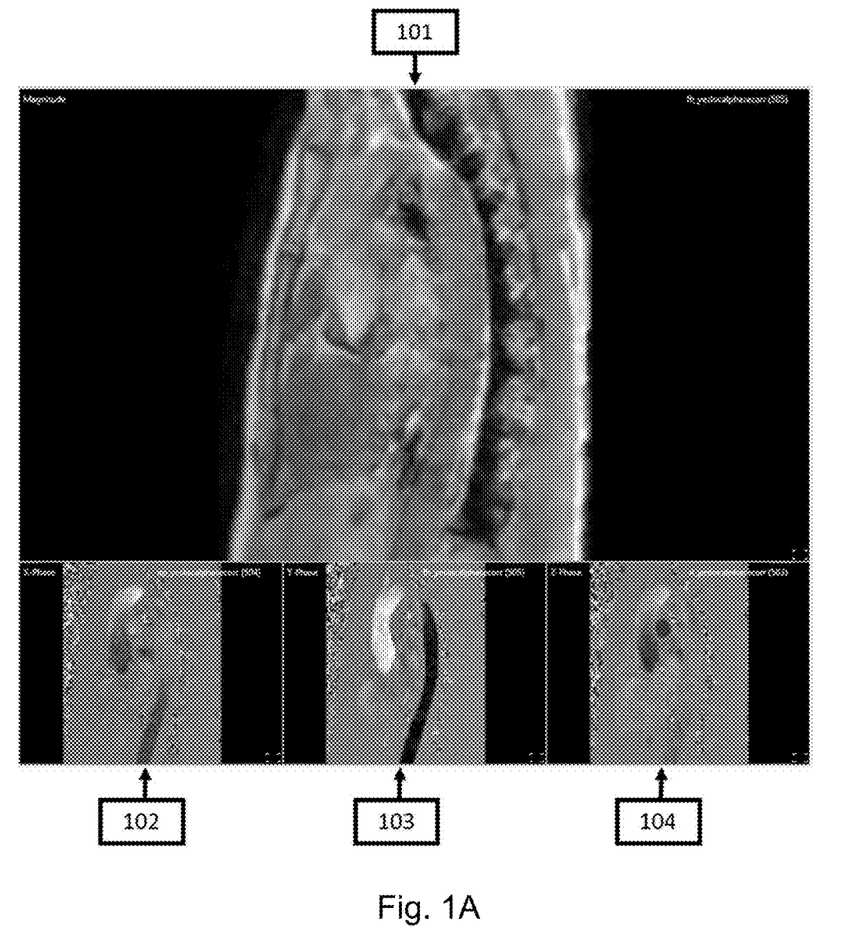
FIG. 1A is a representation of 4D MR Flow data where 101 is the magnitude data and 102-104 the three velocity components.
Figure 1B:
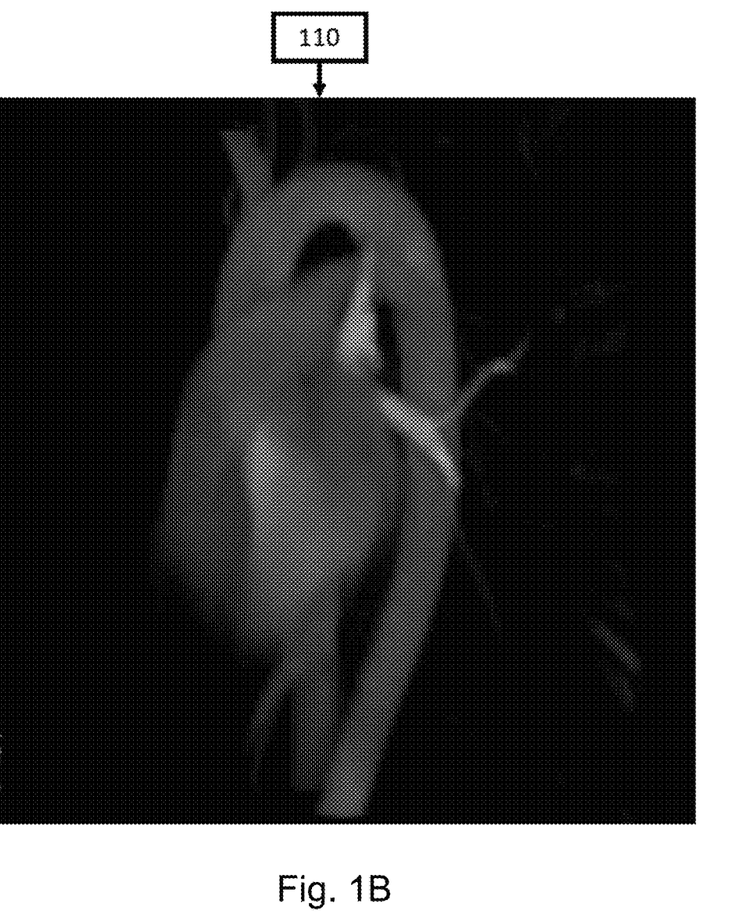
FIG. 1B is a 3D representation of the combined 4D MR Flow data as shown in FIG. 1A.
Figure 2A:
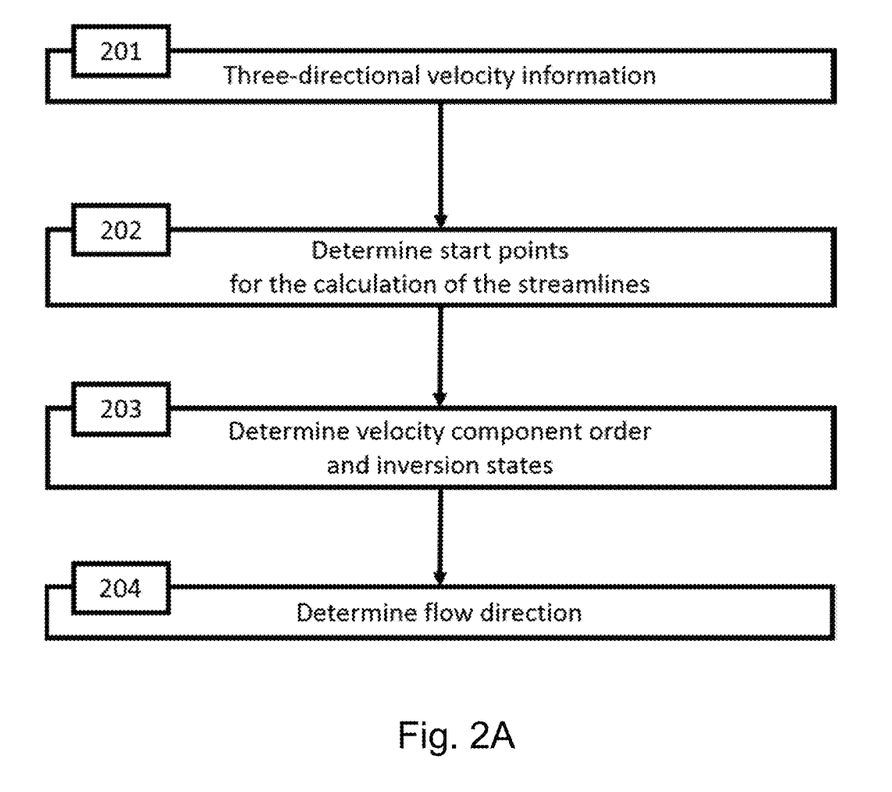
FIG. 2A shows a method for determining velocity encoding direction performed in accordance with an embodiment.
Figure 2B:
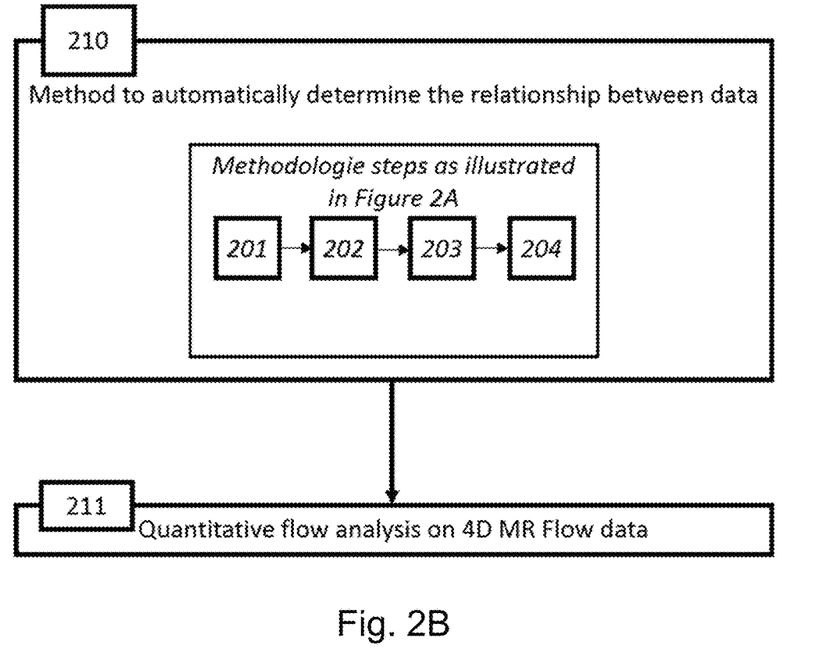
FIG. 2B shows a method for determining velocity encoding direction performed in accordance with an alternative embodiment.

The MM system 702 acquires 4D MR Flow data of a volume of interest for instance the heart and the aorta as shown in FIGS. 1 and 2. The MR system typically includes a magnet system, a radio frequency system, a gradient system, a data acquisition system and a data storage.

The data analysis module 703 may be realized by a personal computer, workstation or other computer processing system. The data analysis module 703 processes the acquired 4D MR Flow data of the MM system 702 to generate, for instance, flow analysis quantification.

The user interface module 701 interacts with the user and communicates with the data analysis module 703. The user interface module 701 can include different kinds of input and output devices, such as a display screen for visual output, a touch screen for touch input, a mouse pointer or other pointing device for input, a microphone for speech input, a speaker for audio output, a keyboard and/or keypad for input, etc.

An embodiment is implemented by the MR system of FIG. 6 as follows. A clinician or other user acquires an MR image of a patient 601 and stores this image on a hard disk 604 or a PACS server 605 in DICOM format.

When storing the image, certain information about the order and the flow direction of the acquired velocity components has become missing making the data useless for, for instance, flow quantification. This is particularly true if DICOM format is used.

FIG. 2A shows a flow chart illustrating the operations according to an embodiment of the present application to restore such information. This represents a suitable set of operations for use with time resolved three-dimensional, three-directional velocity data (i.e. 4D MR Flow data) and is described in order to provide a thorough understanding of various disclosed embodiments.

The operations, typically performed by the data analysis module 703, can also be carried out by software code that is embodied in a computer product (for example, an optical disc or other form of persistent memory such as a USB drive or a network server). The software code can be directly loadable into the memory of a data processing system for carrying out the operations of FIG. 2A.

At 101, the processing system receives time resolved three-dimensional data information (three-dimensional data over time). 4D MR flow consists of anatomical data (101 in FIG. 1A) and three-directional velocity components $V_0$, $V_1$ and $V_2$ (102, 103 and 104 in FIG. 1A) acquired for each pixel within a 3D volume over time. Each voxel within a velocity component represents a positive or negative velocity value in the X, Y or Z direction of that component. In this type of data, the blood flow through each voxel within the acquired volume can be assessed and handled as a 3D directional velocity vector. The spatial size and orientation of all four volumes (101, 102, 103 and 104 in FIG. 1A) are the same and are normally acquired during a single MRI acquisition protocol.

Figure 3:
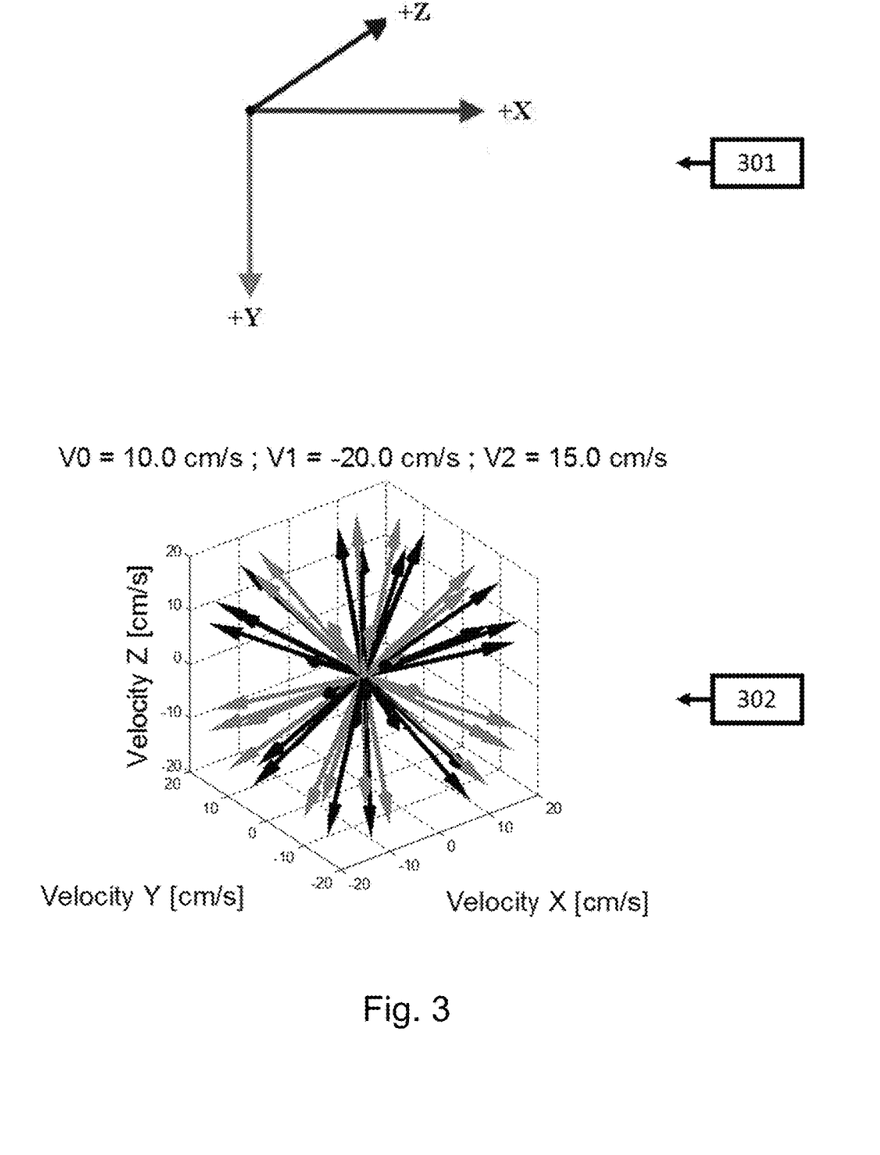
FIG. 3 shows a representation of a right-handed Cartesian coordinate system (301) and all possible velocity vectors that can be obtained by combining the three velocity components (302).

The velocity vectors are acquired as three mutually perpendicular components of each voxel acquired within the 3D volume (102, 103 and 104 in FIG. 1A). These three velocity components, when combined, provides the actual velocity vector of each voxel. To combine correctly, there's the need to know which velocity component is to be positioned on the X, Y or Z axis of the coordinate system. A visual representation 110 of the 3D volume resulted from the three velocity components is shown in FIG. 1B. The magnitude of this velocity vector (defined as S by formula 1) is defined as the absolute velocity of a specific voxel within the 4D MR Flow data. The following described method is based on a right-handed Cartesian coordinate system (see the upper part of FIG. 3 referenced as 301) in which case velocity vectors are represented as:

$$S = |\vec{V}| = \sqrt{V_X^2 + V_Y^2 + V_Z^2} \quad (1)$$

where $V_X$, $V_Y$ and $V_Z$ are the velocity components corresponding to the x-, y- and z-direction of the velocity vector respectively.

The three acquired velocity components $V_0$, $V_1$ and $V_2$ must represent the correct axis of the right-handed Cartesian coordinate system (here termed 'order') and for each velocity component the sign (plus or minus) has to be determined such that the orientation of the resulting velocity vector is conform the same Cartesian coordinate system of equation (1).

There are 6 possible combinations of the three velocity components, namely:

$$\vec{V}_o = \begin{cases} [V_0, V_1, V_2], & o = 0 \\ [V_0, V_2, V_1], & o = 1 \\ [V_1, V_0, V_2], & o = 2 \\ [V_1, V_2, V_0], & o = 3 \\ [V_2, V_0, V_1], & o = 4 \\ [V_2, V_1, V_0], & o = 5 \end{cases} \quad (2)$$

where parameter o indicates the selected order of the components.

Furthermore, one or more of the three velocity components might also require inversion of the flow direction, i.e. change of sign of the velocity component, to form the desired right-handed XYZ velocity vector. There are 8 possible combinations of inversion for the three velocity components. One of these 8 inversion states can be selected with the following inversion function:

$$inv(\vec{V}, i) = \begin{cases} [V_X, V_Y, V_Z], & i = 0 \\ [-V_X, V_Y, V_Z], & i = 1 \\ [V_X, -V_Y, V_Z], & i = 2 \\ [-V_X, -V_Y, V_Z], & i = 3 \\ [V_X, V_Y, -V_Z], & i = 4 \\ [-V_X, V_Y, -V_Z], & i = 5 \\ [V_X, -V_Y, -V_Z], & i = 6 \\ [-V_X, -V_Y, -V_Z], & i = 7 \end{cases} \quad (3)$$

where function inv is applied to indicate a specific inversion combination i of the velocity components.

In total, there are 48 (=6*8) possible combinations of the three acquired velocity components $V_0$, $V_1$ and $V_2$. The lower part of FIG. 3, referenced as 302, is an example showing all these 48 possible vectors. The opposite flow direction of a velocity vector with flow inversion parameter i is given by:

$$inv(\vec{V}, i) \xrightarrow{opposite\ flow} inv(\vec{V}, 7-i) \quad (4)$$

The aim is to extract the correct order of encoding directions of the velocity components and the inversion states.

Reverting to FIG. 2A, at 202, the processor determines suitable reference points also called hereinafter start points as they represent a position in the velocity data from where streamline calculations are initiated.

Useful start points can be indicated by manual positioning points within blood flow locations, for instance proximal and distal positions in one or more vessels of interest. An alternative way is to determine these start points automatically.

An example to determine suitable start points in an automatic way is described herein. The 4D MR Flow data is subdivided into cubes with a specific size. The size can be for example fixed or based on the magnitude of the voxel dimensions from the 4D MR Flow data. Within each subdivided cube, the voxel which contains the maximum absolute velocity will be selected as start point. To avoid the inclusion of points corresponding to noise or with low flow, only voxels are selected where the absolute velocity is above a certain threshold and/or the corresponding voxel in the magnitude data is above a certain magnitude threshold. For the velocity threshold, this should be for instance a factor (between 0 . . . 1) of the maximum absolute velocity within the entire 3D peak systolic data. A typical value for of this factor is ¼. For the magnitude threshold, this should be for instance a factor (between 0 . . . 1) of the maximum magnitude value within the entire 3D peak systolic magnitude data. A typical value for the magnitude factor is ¼. The peak systolic phase may be extracted from the DICOM information or estimated based on the acquired velocity information within the 4D volume (3D volume+time), for instance by identifying the phase (time) in which the absolute velocity is maximum within the 4D volume.

At operation 203, for each of the start points, found during the previous operation, streamlines are calculated by the processor. Streamlines are field lines resulting from the velocity vector field description of the flow. These field lines represent a path of a particle such that the tangent at any point indicates the direction of the velocity of a particle of the fluid at that point. A suitable method for streamline calculation can be based on the Euler integrator method with fixed step size. This method is described in "*Numerical Recipes in C: The Art of Scientific computing,*" 1992 4.2: 136-139 published by the "Press Syndicate of the University of Cambridge".

Figure 4:
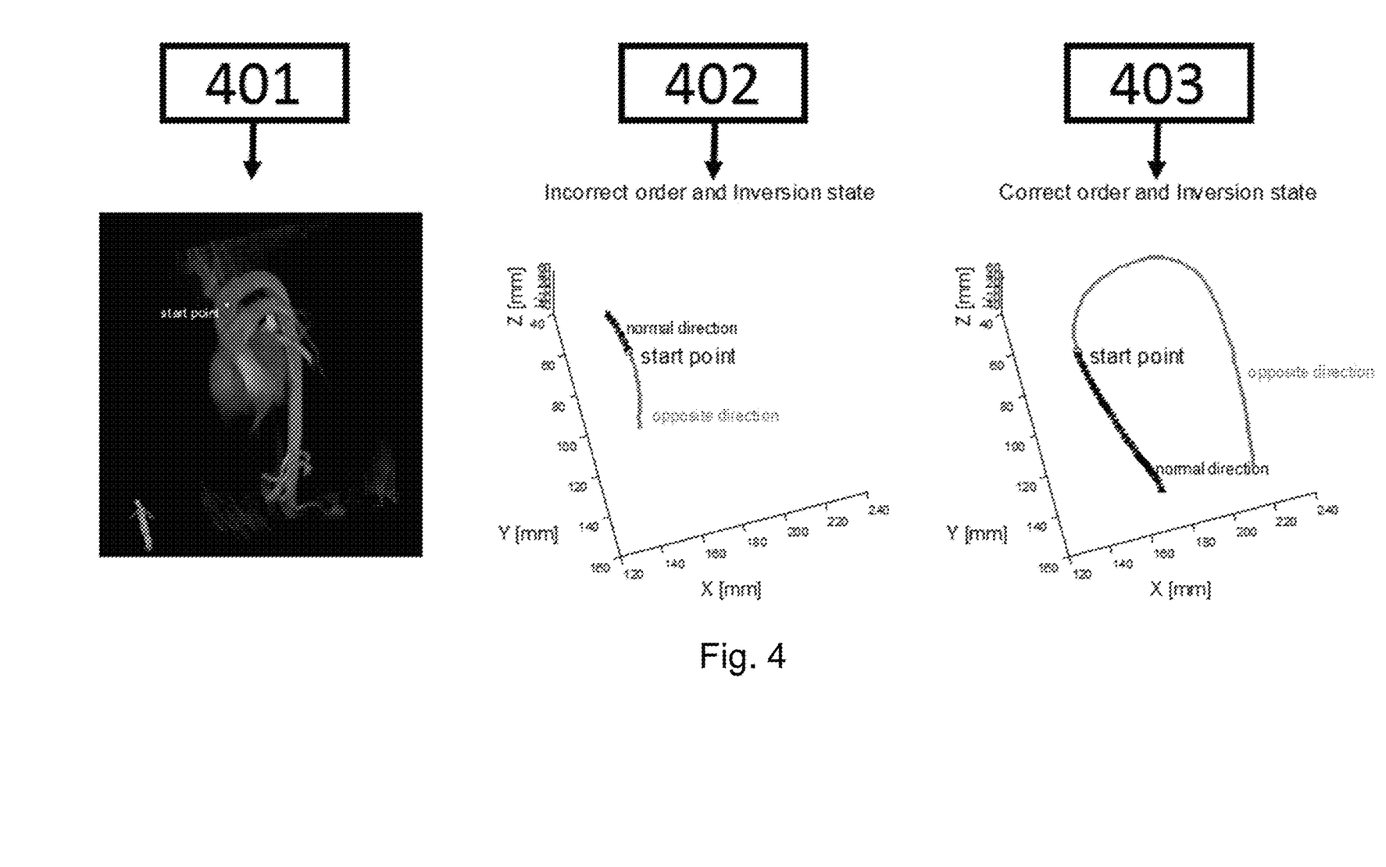
FIG. 4 shows for one start point, the calculated streamlines with the incorrect order and inversion state (402) and the streamlines with the correct order and inversion state (403).

The streamlines are calculated for all 6 combinations of component order and all 8 inversion states. This results in 48 streamlines per point. These streamlines are preferably calculated by the processor for all start points in the peak systolic phase since during that phase the blood flow will be the highest. Within FIG. 4 (reference 402 and 403), the normal direction represents the streamline obtained from one of the first four inversion states i as defined in equation 3. The opposite direction represents the streamline obtained from the inverted inversion states used for the normal direction. FIG. 4 is an example which shows for one start point, the calculated streamlines where an incorrect component order and inversion state is used (see ref 402) and streamlines where a correct component order and inversion state is used (see ref. 403). The streamlines are represented within a three-dimensional graph (X, Y and Z direction in 402 and 403). The start point used in this example is positioned in the ascending part of the aorta as shown in 401. Each graph shows the normal flowing streamline (black line) and opposite flowing streamline (light grey). For each graph, the total length is calculated as the sum of the normal flowing streamline and opposite flowing streamline. The combination of o and i for which the combined streamline length (the sum of the normal flowing streamline and opposite flowing streamline) is maximal will be identified as the correct order $o_{max}$ and inversion state $i_{max}$, where $i_{max}$ represents the normal and opposite inversion state.

The determination of the actual inversion state i or 7−i is explained within operation 204 of FIG. 2A.

To such extent, at 204 the processor determines if the flow direction of inv($\vec{V}_{o_{max}}, i_{max}$) is from proximal to distal. If this is not the case then the flow direction has to be inverted.

Inversion of the velocity vector, i.e. the direction of all 3 velocity components is inverted, results in opposite flow. Hence, the last four inversion combinations (i∈[4,7]) are the opposite flow of the first four inversion combinations (i∈ [0,3]) of equation (3).

An alternative way to determine the flow direction of inv( $\vec{V}_{o_{max}}, i_{max}$) from proximal to distal, is by manual indication of the flow direction in one or more vessels of interest. An example to realize this is by manual positioning a proximal and distal point within a vessel. By this, it is known that the streamline started from the proximal point(s) must be in the direction of the distal point(s). When this streamline with inversion state inv($\vec{V}_{o_{max}}, i_{max}$) is to the distal direction, then the correct inversion is used, otherwise the inversion inv( $\vec{V}_{o_{max}}, 7-i_{max}$) is applicable.

A further alternative way to check the flow direction is by using the pulse wave velocity (PWV). PWV is defined as the velocity at which the arterial pulse propagates and is a measure of arterial stiffness. Within an artery, it is known that the arterial pulse of the distal side (for instance descending aorta) arrives later then the proximal side (for instance ascending aorta). For instance, the pulse wave velocity could be derived as published by Westenberg et. al., *"Improved aortic pulse wave velocity assessment from multislice two-directional in-plane velocity-encoded magnetic resonance imaging,"* JMRI 2010, 32:1086-1094. This processing can be applied on one or more starting points as determined in operation 202.

Figure 5:
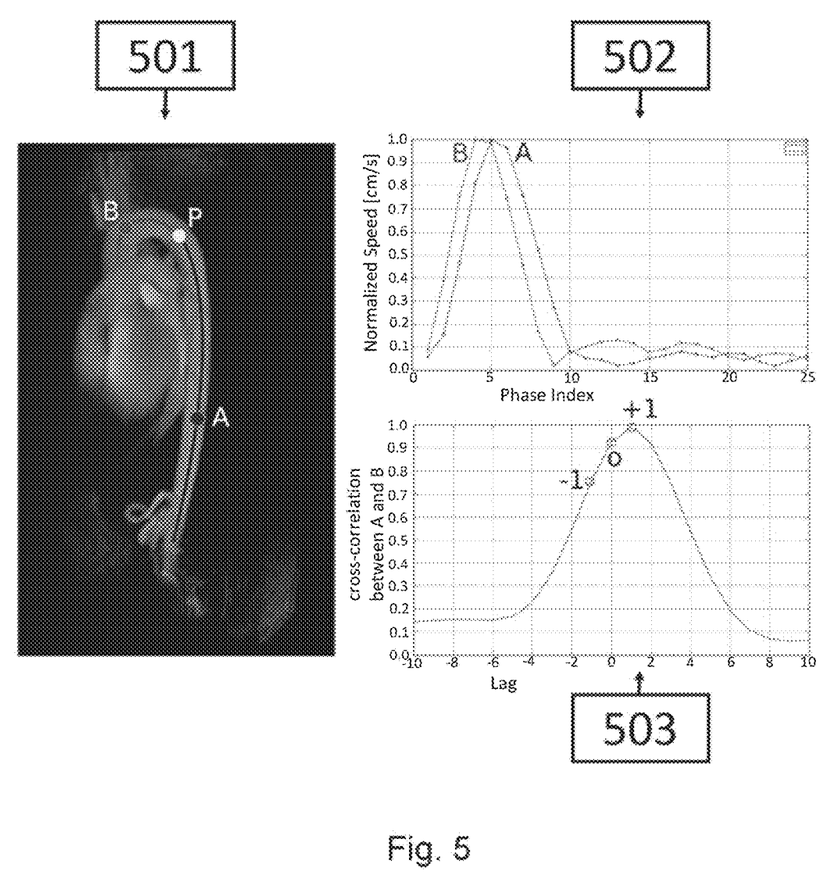
FIG. 5 shows the representation of the pulse wave velocity at two locations on a streamline.

The graph in 502 of FIG. 5 shows the temporal velocity curves within a cardiac cycle for a distal position A and a proximal position B (see 501 in FIG. 5). Hence, the systolic peak of the temporal absolute velocity profile, as defined of the maximum in the velocity graph 502 of FIG. 5, should occur later at downstream (distal) positions than at upstream (proximal) positions. In the example of graph 502 in FIG. 5, the peak systolic phase of position A is downstream related to position B. Position A and B are obtained on the voxel at the streamline started from P (501) with inversion state inv( $\vec{V}_{o_{max}}, i_{max}$) and one on the voxel on the streamline started from P with inversion state inv($\vec{V}_{o_{max}}, 7-i_{max}$). This results in profile A and B as depicted in 502 of FIG. 5. These profiles are taken at the last position along the streamline that still fulfils:

$$S_{profile} = \max(f_{profile} \cdot |\vec{V}(\vec{C}_{start})|, S_{min}) \quad (5)$$

where $f_{profile}$ (value within range [0 . . . 1]) with typical value of 0.625 determines the fraction of the start absolute velocity that will be applied to determine the location where the profiles will be obtained (see point A and B in FIG. 5).

To determine if profile A is upstream or downstream of profile B, a cross-correlation may be used. Cross-correlation is applied to determine if profile A is upstream or downstream of profile B. The cross-correlation function is given by:

$$CC(T) = \sum_{t=0}^{N_{phases}-1} S_A(t) \cdot S_B(\mathrm{mod}(t+T, N_{phases})) \quad (6)$$

where T is the temporal lag,
t is the phase index, and
$N_{phases}$ is the number of phases.
$N_{phases}$ is defined as the amount of 3D volumes within the 4D MR Flow data, and phase index is defined as the index identification a 3D volume within the 4D MR Flow data. Temporal lag is defined as the delay between the two temporal velocity curves. The typical result of the cross-correlation of 2 velocity profiles can be seen in the graph 503 of FIG. 5. At least the cross-correlation for the temporal lags −1, 0 and +1 is calculated. It will be checked if these values are on an up-slope of the correlation function (as can be seen in graph 503 of FIG. 5), hence $$CC(-1) < CC(0) < CC(+1) \quad (7)$$

or on a down-slope, i.e.:

$$CC(-1) > CC(0) > CC(+1) \quad (8).$$

This is done for one or more starting points as determined in step 202 of FIG. 2A. All correlation coefficients that fulfil equation (7) are summed in $N_{UP}$ and all correlation coefficients that fulfil equation (8) are summed in $N_{DOWN}$. When $N_{UP} < N_{DOWN}$, the inversion state inv($\vec{V}_{o_{max}}, 7-i_{max}$) is applicable, otherwise the inversion state (inv($\vec{V}_{o_{max}}, i_{max}$).

At 211, the data analysis module 703 uses the defined order and inversion direction combined with the 4D MR Flow data for further processing to allow visualization and quantification of blood flow. Various visualization and quantification parameters are possible as for instance described by Markl et. al., *"Comprehensive 4D velocity mapping of the heart and great vessels by cardiovascular magnetic resonance,"* J Cardiovasc Magn Reson, 2011, 13(1). Examples of visualization are visualization of streamlines, pathlines, vector fields, cross sectional flow. Examples of quantification are wall shear stress, pressure drop, forward flow, backward flow, regurgitant flow, cardiac output, stroke volume, pulse wave velocity.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A method for determining velocity encoding direction of volumetric image data sets comprising three-directional velocity information comprising three velocity components (V0, V1, V2) of a target volume, the method comprising:
   a) defining a coordinate system comprising three coordinate axes (X, Y, Z);
   b) determining all the possible arrangements of the three velocity components (V0, V1, V2) along the three coordinate axes (X, Y, Z);
   c) determining reference point or points in the target volume either automatically or upon user input;
   d) determining streamlines for each reference point for all of the possible arrangements of the three velocity components as determined in b); and
   e) considering, as the velocity encoding direction, the arrangement of the three velocity components corresponding to the streamline having the longest length or a length above a threshold.

2. The method of claim 1, wherein:
flow direction is used to determine the orientation of the velocity encoding direction, such flow direction being user input or automatically calculated.

3. The method of claim 2, wherein:
the arrangement of the three velocity components is inverted in orientation if the corresponding flow line doesn't follow the flow direction.

4. The method of claim 1, wherein: at least one reference point is determined by selecting velocity voxels having velocity module above a velocity threshold.

5. The method of claim 1, wherein:
the volumetric image data sets comprise structural magnitude information and three-directional velocity information of the target volume; and
at least one reference point is being determined by selecting magnitude voxels having magnitude data above a magnitude threshold.

6. The method of claim 1, wherein:
temporal velocity curves in a point upstream (A) and in a point downstream (B) are used to determine the flow direction, the flow direction being considered downstream if the curve at point upstream (A) is delayed in time with reference to the curve at point downstream (B), and the flow direction being considered upstream if the curve at point downstream (B) is delayed in time with reference to the curve at point upstream (A).

7. The method of claim 6, wherein:
delay between the curves is searched by identifying the peak in the curves and comparing temporal position among such peaks.

8. The method of claim 6, wherein:
delay between the curves is searched by calculating a correlation function among the upstream and downstream curves.

9. The method of claim 8, wherein:
the correlation function is given as:

$$CC(T) = \sum_{t=0}^{N_{phases}-1} S_A(t) \cdot S_B(\mathrm{mod}(t+T, N_{phases}))$$

where $S_A$, $S_B$ are, respectively, velocity curves at upstream point A and at downstream point B, T is a temporal lag between the velocity curves, t is a phase index identifying a 3D volume within a 4D flow data set, and $N_{phases}$ is a number of phases corresponding to a number of 3D volumes within the 4D flow data set, the correlation function being calculated at least for three lags comprising −1, 0, +1, wherein upstream condition is determined if $CC(-1) < C(0) < CC(+1)$ or downstream condition is determined if $CC(-1) > CC(0) > CC(+1)$.

10. The method of claim 1, further comprising:
performing quantitative flow analysis using the velocity information and/or showing streamlines, vector fields, cross sectional flow or similar parameters.

11. The method of claim 1, wherein:
the image data sets are sequences of 4D MR flow data sets.

12. The method of claim 1, wherein:
volumetric image data sets are related to one or more cardiac cycles, streamlines and/or velocity curves being determined in the peak systolic phase of such cycle or cycles.

13. A computer product directly loadable into the memory of a digital computer and comprising a non-transitory computer readable medium storing software code portions for performing the method according to claim 1 when the computer product is run on a computer.

14. An MR apparatus for acquiring volumetric images, the apparatus comprising an acquisition system for obtaining a cine of consecutive image volumes of a target organ, the apparatus further comprising a processing module programmed for performing the method according to claim 1.

15. The MR apparatus of claim 14, wherein:
the acquisition system is configured to acquire 4D flow images of a volume containing a vessel; and
the processing module is programmed to determine the direction and orientation of the velocity vectors related to the flow within such vessel with reference to a coordinate system.

16. The MR apparatus of claim 15, wherein:
the orientation of velocity vectors is determined by the processing module by calculating pulse wave velocity curves in at least two points of the vessel and determining the temporal shift between such curves.

* * * * *